United States Patent [19]

Vassiliades

[11] Patent Number: 4,879,134

[45] Date of Patent: Nov. 7, 1989

[54] FINGERPRINTING COMPOSITIONS, SYSTEMS AND METHODS

[76] Inventor: Anthony E. Vassiliades, 8738 Tanager Woods Dr., Cincinnati, Ohio 45249

[21] Appl. No.: 253,941

[22] Filed: Oct. 5, 1988

Related U.S. Application Data

[63] Continuation of Ser. No. 938,420, Dec. 5, 1986, abandoned.

[51] Int. Cl.$^4$ .......................... A61B 5/10; B41K 1/00; C09D 11/00
[52] U.S. Cl. .......................................... 427/1; 106/22; 118/31.5
[58] Field of Search ............... 106/21, 22; 427/1, 150, 427/151; 118/31.5

[56] References Cited

U.S. PATENT DOCUMENTS

| | | | |
|---|---|---|---|
| 3,423,427 | 1/1969 | Cescon et al. | 106/22 |
| 3,560,229 | 2/1971 | Farnham et al. | 106/22 |
| 3,597,244 | 8/1971 | Fookson et al. | 106/22 |
| 4,108,671 | 8/1978 | Richlin | 106/22 |
| 4,171,982 | 10/1979 | Lin | 106/22 |
| 4,334,015 | 6/1982 | Yarian | 106/21 |
| 4,372,583 | 2/1983 | Vassilliades | 427/150 |

OTHER PUBLICATIONS

*Research Disclosure* (Jul. 1973), p. 42.

*Primary Examiner*—Janyce Bell
*Attorney, Agent, or Firm*—Sigalos, Levine & Montgomery

[57] ABSTRACT

A self-contained liquid composition for use in making fingerprints comprising the reaction product of at least one leuco or non-leuco chromogenic compound and at least one color-developing substance in a liquid vehicle that is a solvent for said chromogenic compound and reaction product and a solvent or dispersant for said color-developing substance. The method of fingerprinting and a fingerprinting system utilizing the liquid composition are also disclosed.

13 Claims, No Drawings

FINGERPRINTING COMPOSITIONS, SYSTEMS AND METHODS

This application is a continuation of application Ser. No. 938,420 filed Dec. 5, 1986, now abandoned.

BACKGROUND OF THE INVENTION

The present invention relates to inkless fingerprinting systems used for identification purposes. More specifically, it relates to compositions, systems, and methods of generating instant, stable fingerprints on various substrates without the need of conventional inks and specially treated surfaces, and without the use of any chemical or mechanical post-treatment of the fingerprint or the surface on which the fingerprint was made.

As used herein the term "fingerprints" also encompasses "footprints" such as those taken of newly-born infants and placed on birth records. Also, the term "inkless" means the absence of colored pigments such as carbon black and as being distinct from printing inks as such term is now understood in this art.

The fingerprint patterns or ridge endings and ridge separations are highly individualized and are not altered with time. The comparison of fingerprint patterns has long been accepted as an absolute means of identifying individuals in a multitude of criminal and non-criminal situations.

In order for a fingerprinting identification system to be commercially acceptable it must be extremely stable and reliable, i.e., the prints must be distinct and clear and must be easily readable by the human eye and by automated fingerprint reading systems which are finding increased usage especially with a number of law enforcement agencies. Furthermore, the prints must form instantaneously, and must possess a high degree of stability toward exposure to extreme atmospheric conditions such as temperature, humidity and light. Preferably, the systems must be simple and aesthetically inoffensive.

Traditionally, fingerprints have been made with printing or writing types of ink, usually comprising finely ground carbon black particles dispersed in a liquid vehicle. The carbon black dispersion is ordinarily applied to a flat and firm surface, the excess dispersion removed, transferred to the surface of the object to be fingerprinted or identified, and subsequently transferred to the surface of the substrate where the final print is to be made. Such a procedure is cumbersome, time consuming and results in severe soiling of the hands and clothing of everyone involved in the fingerprinting process.

During the past several years inkless fingerprinting systems have been proposed such as disclosed in U.S. Pat. No. 3,831,552 involving the use of magnetizable powders. Other proposed inkless systems utilize the chelation of specific metal salts such as sodium vanadate with organic acids as described in U.S. Pat. No. 2,082,735, or various methods of reacting 8-hydroxyquinoline with metal salts, and preferably ferric chloride, as described in U.S. Pat. Nos. 3,960,632, 4,262,623, and 4,379,178. Additionally, U.S. Pat. No. 4,232,083 discloses the use of metal complexing compounds having a plurality of ligand groups with transitional metal salts of oleophilic, organic acids to form dark images which can be useful in fingerprinting systems.

The inkless fingerprinting systems known heretofore possess varying degrees of undesirable properties. Some are mechanically too complex to find commercial application and others, especially those relying upon metal-chelation reactions, are usually too slow and the image of the fingerprint does not appear instantaneously and in some cases it takes long periods of time before the print develops its full intensity. Oftentimes, these slow-forming inkless fingerprinting systems can be rendered completely inoperable if fingerprinting is attempted in substantially lower than ambient temperature as would be the case in an outdoor environment in geographic locations with extremely cold climates.

All of the known inkless fingerprinting systems require at least two separate steps. That is, the incorporation of one of the reactive components in one medium such as a fingerprinting pad and the chemical or mechanical pre-treatment of the substrate, usually paper, where the final fingerprint appears. In some cases, the fingerprint is treated chemically or mechanically after it is made in order to develop its desired color and color intensity.

SUMMARY OF THE INVENTION

It has now been discovered that totally self-contained, inkless fingerprinting system can be provided which systems produce clear and extremely stable fingerprints on a number of substrates without requiring a separate treatment of the substrate. The fingerprints of the present invention are formed instantaneously, they possess extremely high color intensity and are stable even after prolonged periods of exposure to atmospheric conditions.

Briefly stated, the present invention comprises a liquid composition for use in making fingerprints comprising the reaction product of at least one leuco or non-leuco chromogenic compound and at least one color-developing substance in a liquid vehicle that is a solvent for said chromogenic compound and reaction product and a solvent or dispersant for said color-developing substance.

The invention also comprises a fingerprinting system as hereinafter described.

DETAILED DESCRIPTION

The essential components of the instant fingerprinting compositions are the chromogenic compounds, color-developing substances, and the liquid vehicle.

The chromogenic compounds are leuco dye intermediates which possess the unique property of being colorless in neutral or alkaline media, but become colored when they react with an acidic or electron accepting substance. These dyes are, per se, well known and examples thereof which can be used in this invention are crystal violet lactone (CVL), dilactones, benzoyl leuco methylene blue (BLMB), derivatives of bis-(p-dialkylaminoaryl) methane, xanthenes, indolyls, auramines, fluorans and bisfluorans such as those described in U.S. Pat. Nos. 2,981,733, 2,981,738, 669,711, 3,681,390, 3,819,396, 3,821,010 and 4,302,393. Additionally, non-leuco, oil-soluble dyes such as Keystone Aniline's Keysolv Black RBM, Keysolv Yellow R, DuPont's Oil Orange B Liquid, Oil Blue B Liquid Dye, Oil Red B Liquid, Oil Yellow Liquid, and Oil Green Liquid Dye, may be used in this invention. The preferred dyes of the present invention, however, are the leuco chromogenic compounds.

There is a multitude of known electron-accepting color-developing substances capable of reacting with the leuco chromogenic compounds, which can be used in the present invention, and which have been described in the prior art. Among such electron-accepting substances are acidic clays such as montmorillonites, kaolins, bentonites and attapulgites, low molecular weight phenol-aldehyde condensation products (novolaks) and/or their metal salts as disclosed in U.S. Pat. Nos. 3,427,180, 3,672,935, and 3,723,156, and derivatives of aromatic carboxylic acids and/or their metal salts as disclosed in U.S. Pat. Nos. 3,488,207, 3,864,146, 3,871,900, 3,934,070, 3,983,292, 4,303,719, and 4,372,583. Specific examples of such color-developing materials usable in the present invention are: 3-phenyl salicylic acid, 3,5-di-tertiary butyl salicylic acid, octyl salicylic acid, 2-hydroxy-1-benzyl-3-naphthoic acid, 2-hydroxy-4-methyl-5-isobutyl thiobenzoic acid, 3,3'-thiobis (2-hydroxy-5-methyl) benzoic acid, 2-hydroxy-5-butyl sulfonyl benzoic acid, condensation products of salicylic acid and salicylic acid derivatives, United Catalyst's Copisil, a montmorillonite clay, low molecular weight condensation products of p-phenyl phenol with formaldehyde, p-cyclohexyl phenol-formaldehyde condensation product, and p-tertiary-amylphenol-formaldehyde condensation product.

Critical to the instant invention are the careful selection of the type and amount of the chromogenic compounds, their controlled coupling with the various color-developing substances, and the physical and chemical properties of the solvent. The type of chromogenic compound selected will determine the hue or color of the final print or image and the amount of the chromogenic compound must be balanced with the amount of the color-developing substance used to ensure the desired final intensity, speed, and stability of the final print or image. The solvent used with any particular combination of chromogenic compound(s) and color-developing substance(s) must possess good solvating or dispersing properties for the components to be dissolved and/or dispersed in the solvent, give good flow properties for easy and complete transfer of the composition from the pad to the finger and from the finter to the substrate, and have low evaporation rate for prolonged shelf-life in the fingerprinting pad. Moreover, the acidity; or lack of it, of the solvent used can affect the exact hue of the final print or image depending upon the chromogenic compound used.

However, by operating within the parameters disclosed herein, one skilled in this art can by routine experimentation determine for any particular chromogenic compound the most suitable color-developing substance and solvent and proportions thereof to give the desired final hue or color and a final print having the desired intensity and stability.

The solvents used in the present invention must possess good solvating characteristics for the dyes and the color-developing substances to enable and enhance the reaction between the two materials, except when the color-developing substance is an activated clay or a similar pigment in which case only dispersability of the color developer in the solvent is required. Additionally, the solvents to be used in the self-contained fingerprinting systems of the instant invention must have low evaporation rates for prolonged shelf life in the pad, good flow properties for rapid and complete transfer from the pad to the finger and from the finger to the substrate, be clear in color to avoid interference with the final hue of the fingerprint, and exhibit no adverse toxicological effects. Exemplary of the solvents in this invention are alkylated phenols such as monoisobutyl biphenol and monoisopropyl biphenol, chlorinated paraffins, alkylated naphthalenes, partially hydrogenated terphenyls such as Monsanto's HB-40, soya bean oil, cottonseed oil, coconut oil, ester alcohols such as Eastman Kodak's Texanol, alkylated glycol ethers and ether acetates such as Eastman Kodak's Ektasolve series, and combinations thereof.

In accordance with this invention, fingerprints of almost any color can be produced; the preferred color, however, is black.

In one mode of this invention, the self-contained, inkless fingerprinting solution is prepared by dissolving the leuco dye in a solvent and subsequently reacting them with amounts of the electron-accepting or color-developing substance sufficient to acidify the particular dye used; a stoichiometric amount usually being sufficient, by dissolving or dispersing such color-developing substances in the same solution containing the leuco dyes. The dye and color-developer react under ambient conditions of temperature and pressure. A fingerprinting system, usually comprising a container housing means capable of releasably retaining a fluid (such as any conventional felt or blotter material pad now conventionally used for fingerprinting) is impregnated with the self-contained inkless solution. Clear and stable fingerprints can be made with this pad without soiling the fingers; the solution is removed from the finger when the finger is applied to the substrate, usually paper, on which the print is to be retained.

In another mode of the present invention, the self-contained, inkless fingerprinting solution is prepared by sequentially dissolving the leuco dye(s) and the color developer(s) in the same solvent and adding small amounts of metallic ions such as zinc, cadmium, nickel, aluminum, magnesium, and manganese in the form of salts to the solution prior to impregnating the pad. The addition of the metallic ions seems to catalyze the dye-color developer reaction and significantly increase the intensity and the rate of appearance of the final fingerprint. Furthermore, since the metallic ions themselves are electron-accepting species they can act as the sole color-developing substances in this invention. It is preferable, however, to use them in combination with one or more of the other color-developing substances described earlier.

In still another mode of this invention, it has been surprisingly found that when the self-contained, inkless fingerprinting solution is produced by coreacting in the same solvent the leuco dyes, the color-developing substances and the metallic ions and followed by the addition of small amounts of aqueous or liquid ammonia, the color of the solution fades significantly and yet the solution produces fingerprints extremely rapidly of high intensity and stability. This is especially true when the metallic ions employed are zinc, cadmium, nickel, aluminum, tin, titanium, magnesium, or manganese. While not completely understood, a possible explanation for such a phenomenon is the fact that some of these metallic elements such as zinc and cadmium, for example, are known to form hydroxyl and ammonia containing anion complexes which can be described as $[M(NH_3)_x]--$, where M is the metal and x is the complex co-ordination number of the metal. These complexes are known to have limited stability, especially under hydrolytic conditions, and this fact coupled with the "bleaching" effect of ammonia toward leuco dyes (leuco dyes by definition are colorless in neutral or alkaline media) could explain this surprising and highly desirable behavior of the inkless fingerprinting solutions of this invention which contain ammonia and metallic ions. It can be presumed that any other compound capable of forming complexes of low stability in alkaline media with the metallic ions could be used in lieu of ammonia and still produce the same favorable effects in the instant invention.

In still another mode of the present invention, the inkless fingerprinting solution is prepared by sequentially reacting the dissolved leuco dyes with the color developer and the ammonia complex of the metallic salt, and subsequently dispersing in the solution small amounts; about 5 to 20% by weight of inorganic pigments. Inorganic pigments generally possess high refractive indices and the incorporation of such pigments into the inkless fingerprinting solution facilitates the automated reading of the fingerprints by such instruments which rely upon high light refraction and light scattering of the characters which are to be recognized optically. For such purposes, a minor amount of a printing ink; i.e., 1 to 5% by weight can also be added.

In still another mode of this invention, the inkless fingerprinting solutions are produced by utilizing non-leuco, oil-soluble dyes in the oleophilic solvents already set forth above.

During the development of the present invention it has also been found that the addition of small amounts of latexes (natural o synthetic) such as butadiene-styrene acrylic, polyvinyl acetate latexes and the like, along with small amounts of coalescing aides such as ester alcohols and alkylated glycol ether acetates to the inkless fingerprinting solutions, greatly enhances the clarity of the fingerprints made; i.e., there is a sharper image of the prints of the distal ridges. This feature is especially important to the present inkless fingerprinting system since the producer of these self-contained pads will have no control of the surface of the substrate on which the fingerprints will be placed. The properties of paper surfces, the most commonly used substrates for fingerprint taking, can vary widely depending upon type and degree of surface treatment such as surface sizing during paper manufacturing. This, in turn, can affect greatly the degree of oil adsorption by the paper fibers and the diffusion or spreading of the oil within the fibers and thus affect the clarity of the fingerprint. The controlled addition of small amounts of latex-coalescing aide mixtures to the inkless fingerprinting solutions, increases the viscosity of the solution and reduces substantially the risk of producing unclear fingerprints irrespective of the nature and characteristics of the paper surface.

It has also been found during the development of this invention that the addition of small amounts (between 0.5% and 2.0% of the weight of the inkless solution) of ultra violet absorbers such as nickel bis(octyl phenol) sulfide, hydroxy benzophenones, hydroxy benzotriazoles and the like, to the inkless fingerprinting solutions can further improve the stability of the fingerprints during prolonged exposures to light.

The invention will be further described in connection with the examples that follow, which are set forth for purposes of illustration only without intending to limit the scope of the invention.

The following leuco dyes with their respective designation in parentheses were used in the examples and obtained from Ciba-Geigy: Pergascript Black (I-BR), Pergascript Blue (I-2R), crystal violet lactone (CVL), Pergascript Green (I-GD), Pergascript Red (I-6B), and Pergascript Orange (I-5R); Benzoyl Leuco Methylene Blue (BLMB) was obtained from Hilton Davis Chemical Company. Unless otherwise noted, all percentages and parts are by weight.

EXAMPLE 1

A self-contained inkless fingerprinting solution was prepared by dissolving in 40 parts of Monsanto's HB-40 (a partially hydrogenated terphenyl), 2 parts of I-BR, 0.35 parts of CVL, 0.25 parts of BLMB, and 1.2 parts of an oligomeric condensation product of 5-octyl salicylic acid with formaldehyde. Following the dissolution of the dyes and the acid, 5.5 parts of a 16% solution of zinc octoate in mineral spirits were added and the total solution was agitated for 15 minutes.

A fingerprinting pad was impregnated with the solution of this example and black-colored fingerprints of high intensity were made in the conventional manner on a number of different paper substrates using this system. The solution deposited a slightly dark haze on the finger prior to making the fingerprint, but the haze disappeared after impressing the finger on the substrate in making the fingerprint. The fingerprints appeared instantaneously, exhibited good stability during exposure to sunlight for prolonged periods of time, and they possessed good clarity. The degree of clarity, however, varied with changes in the surface pre-treatment of the paper. For example, when fingerprints were made on newsprint, a paper surface this is not normally sized, they had a tendency to diffuse or "feather" upon standing; this resulted in some unclear fingerprints after a while.

COMPARATIVE EXAMPLE 1a

This example illustrates the invention wherein the addition of small amounts of an alkaline substance capable of forming complexes of relatively low stability with the metallic ions used can improve the aesthetics of the self-contained inkless fingerprinting system without interfering with its functionality.

Example 1 was repeated, but a small amount (about 0.4 milliliters) ofaqueous ammonia was thoroughly mixed with the self-contained inkless fingerprinting solution for about fifteen minutes prior to impregnating the pad. Equivalent results to those in Example 1 were obtained with the exception that the slight haze was completely eliminated from the finger even prior to making the fingerprint.

COMPARATIVE EXAMPLE 1b

This example illustrates the invention wherein the addition of small amounts of latex along and coalescing aide can significantly improve the sharpness of the fingerprints.

Example 1 was repeated, but 1.5 parts of a mixture containing 90% Dow Chemical's latex 638 and 10% Eastman Kodak's Texanol (ester alcohol) were added to the self-contained inkless fingerprinting solution and allowed to mix for about one hour prior to impregnating the pad. Equivalent results to those of Example 1 were obtained with the exception that fingerprints made even on newsprint were clear and maintained their clarity indefinitely.

EXAMPLE 2

A pad was impregnated with a self-contained inkless fingerprinting solution which solution was prepared as follows: 4.8 parts of I-BR, 1.5 parts of CVL, 1.0 part of I-6B, 110 part of I-GD, 1.0 part of I-5R, 0.3 part of nickel bis(octyl phenol) sulfide, and 5 parts of 3,5-di-tertiary butyl salicylic acid were dissolved in 30 parts of HB-40 and 30 parts of Texanol. Following complete dissolution of the dyes and the acid, 1.0 part of a 50% aqueous solution of zinc chloride, 16.5 parts of a 16% solution of zinc octoate, 10 milliliters of aqueous ammonium hydroxide, and 2.0 parts of Rohm and Haas' acrylic copolymer emulsion E-2074 were added to the inkless fingerprinting solution and mixed for about 5 minutes.

Black-colored fingerprints with high degree of clarity and stability were produced on a number of different paper substrates using this system.

EXAMPLE 3

Example 2 was repeated, but the 5 parts of 3,5-di-tertiary butyl salicylic acid were replaced with parts of 5-octyl salcicylic acid. Equivalent results were obtained.

EXAMPLE 4

Example 2 was repeated, but the 5 parts of 3,5-ditertiary butyl salicylic acid were replaced with parts of 2-hydroxy-4-methyl-5-isobutyl thio benzoic acid. Equivalent results were obtained.

EXAMPLE 5

Example 2 was repeated, but 5 parts of titanium dioxide were thoroughly dispersed in the solution, using a Waring blender, prior to the addition of the acrylic copolymer emulsion. This resulted in an increase in the viscosity of the solution compared to that of Example 2, but the results obtained were equivalent to those obtained in Example 2.

EXAMPLE 6

A fingerprinting pad containing an inkless printing composition was prepared by first dissolving 5.0 parts of I-BR, 1.0 part of CVL, 1.0 part of I-GD, 1.0 part of I-5R, 1.5 parts of BLMB, 0.5 parts of I-6B and 0.5 parts of nickel bis(octyl phenyl) sulfide in a solution containing 60 parts diethylene glycol monoethyl ether acetate, 40 parts of HB-40, and 8 parts of a low molecular weight p-phenylphenol-formaldehyde condensation product. To this solution, 10 parts of a 16% solution of zinc octoate and 5 milliliters of aqueous ammonia solution wer added along with 3.5 parts of Rohm and Haas' Acryloid NAD-10 resin and mixed for about one hour.

A pad was impregnated with this inkless fingerprinting solution and fingerprints taken. The result was clear, dark green, almost black fingerprints with good stability during prolonged exposures to atmospheric conditions.

EXAMPLE 7

Example 6 was repeated, but the 8 parts of p-phenylphenol-formaldehyde condensation product were replaced with 7 parts of a low molecular weight condensation product of p-tertiary-amylphenol with formaldehyde. The results were equivalent to those of Example 4.

EXAMPLE 8

Example 6 was repeated with the exception that 6 parts of Huber's Hydrasperse-90, a kaolin clay, were thoroughly dispersed in the solution prior to the addition of the 3.5 parts of the Acryloid NAD-10 resin. The results were equivalent to those of Example 4.

EXAMPLE 9

A self-contained inkless fingerprinting solution was prepared by dissolving 3.1 parts of I-BR, 1.0 part of CVL, 3.3 parts of I-GD, 0.8 parts of I-6B, 0.3 part of BLMB and 0.3 part of nickel bis(octyl phenol) sulfide in 92 parts of HB-40 which had dispersed in it 10 parts of Copisil clay. Three parts of a mixture containing 90% Dow's latex 638 and 10% Eastman Kodak's Texanol were added to the dispersion and allowed to mix for about one hour.

A pad impregnated with the solution of this example was used to make black, clear fingerprints on a number of various paper surfaces.

EXAMPLE 10

A self-contained inkless fingerprinting solution comprising 3.0 parts of Keystone Aniline's Keysolv Black RBM and 0.3 parts of Keysolv Yellow R, 0.3 parts of DuPont's Oil Red B Liquid, and 60 parts of HB-40 was prepared.

A pad impregnated with the solution gave clear, purplish-black fingerprints on a number of paper substrates.

EXAMPLE 11

A self-contained inkless fingerprinting solution was prepared by dissolving 4.0 parts of I-BR, 1.0 part of CVL, 0.5 parts of BLMB, 0.3 part of nickel bis(octyl phenol) sulfide and 2.5 parts of 5-octyl salicylic acid in 80 parts of HB-40, 5 parts of monoisobutyl biphenol and 5 parts of Texanol. Subsequently, 1.0 part of a 50% aqueous solution of zinc chloride, 7 parts of a 16% solution of zinc octoate, 2.5 parts of aqueous ammonia and 2.5 parts of Dow's latex 638 were added and allowed to mix for about 30 minutes.

A pad saturated with the solution of this example gave black, clear fingerprints with excellent stability during prolonged exposures toward severe atmospheric conditions of light, temperature and humidity.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A self-contained inkless liquid composition for use in making fingerprints comprising the reaction product of at least one leuco or non-leuco chromogenic compound and at least one color-developing substance, metallic ions, a compound capable of forming complexes of low stability in an alkaline medium with said metallic ions, and a liquid vehicle that is a solvent for said chromogenic compound and reaction product and a solvent or dispersant for said color-developing substance.

2. The composition of claim 1 wherein said chromogenic compound is a leucodye and said color-developing substance is an electron-accepting substance.

3. The composition of claim 1 wherein said chromogenic compound is a non-leuco dye, oil-soluble dye and said solvent is an oleophilic solvent.

4. The composition of claim 2 wherein said electron-accepting substance is selected from acidic clays, low molecular weight phenol-aldehyde condensation products or their metal salts, derivatives of aromatic carboxylyic acids or their metal salts, or mixtures thereof.

5. A method of fingerprinting comprising applying to a member to be fingerprinted the liquid composition of claim 1, 2, or 3 and the applying the member to a substrate to transfer said liquid composition to said substrate.

6. The method of claim 5 wherein said liquid composition is impregnated in a means capable of releasably retaining said composition.

7. A fingerprinting system comprising means capable of releasably retaining a liquid and an inkless liquid composition releasably retained in said means, said liquid composition comprising the reaction product of at least one leuco or non-leuco chromogenic compound and at least one color-developing substance, metallic ions, a compound capable of forming complexes of low stability in an alkaline medium with said metallic ions, and a liquid vehicle that is a solvent for said chromogenic compound and reaction product and a solvent or dispersant for said color-developing substance.

8. The system of claim 7 wherein said chromogenic compound is a leuco dye and said color-developing substance is an electron-accepting substance.

9. The system of claim 7 wherein said chromogenic compound is a non-leuco dye, oil-soluble dye and said solvent is an oleophilic solvent.

10. A self-contained inkless liquid composition for use in making fingerprints comprising the reaction product of at least one leuco or non-leuco chromogenic compound and at least one color-developing substance, metallic ions, ammonia, and a liquid vehicle that is a solvent for said chromogenic compound and reaction product and a solvent or dispersant for said color-developing substance.

11. The composition of claim 10 including a synthetic latex in said composition.

12. A fingerprinting system comprising means capable of releasably retaining a liquid and an inkless liquid composition releasably retained in said means, said liquid composition comprising the reaction product of at least one leuco or non-leuco chromogenic compound at least one color-developing substance, metallic ions, ammonia, and a liquid vehicle that is a solvent for said chromogenic compound and reaction product and a solvent or dispersant for said color-developing substance.

13. The system of claim 12 including a synthetic latex in said composition.

* * * * *

UNITED STATES PATENT AND TRADEMARK OFFICE
CERTIFICATE OF CORRECTION

PATENT NO. : 4,879,134
DATED : November 7, 1989
INVENTOR(S) : Vassiliades, Anthony E.

It is certified that error appears in the above-identified patent and that said Letters Patent is hereby corrected as shown below:

Column 2, line 21, "SUMMARY OF THE INVENTION" should be centered and on a line by itself, line 51, underscore the words -- per se -- line 57, delete "669,711" and insert -- 3,669,711, -- line 58, delete "3819,396" and insert -- 3,819,396 --

Column 6, line 42, delete "ofaqueous" and insert -- of aqueous --.

Column 7, line 10, delete "5" and insert -- 45 --, line 17, after "with" insert -- 5 --.

Column 8, line 61, delete "leucodye" and insert -- leuco dye --.

Signed and Sealed this

Twenty-second Day of January, 1991

Attest:

HARRY F. MANBECK, JR.

*Attesting Officer*    *Commissioner of Patents and Trademarks*